United States Patent
Hannemann et al.

(10) Patent No.: US 12,385,153 B2
(45) Date of Patent: Aug. 12, 2025

(54) APPARATUS AND METHOD FOR UTILIZING OFF-GASES FROM A POWER-TO-X SYSTEM

(71) Applicant: Siemens Energy Global GmbH & Co. KG, Bayern (DE)

(72) Inventors: Frank Hannemann, Rottenbach (DE); Joachim Lamp, Bubenreuth (DE); Gerhard Zimmermann, Höchstadt/Aisch (DE)

(73) Assignee: Siemens Energy Global GmbH & Co. KG, Munich (DE)

( * ) Notice: Subject to any disclaimer, the term of this patent is extended or adjusted under 35 U.S.C. 154(b) by 611 days.

(21) Appl. No.: 17/784,532

(22) PCT Filed: Dec. 15, 2020

(86) PCT No.: PCT/EP2020/086200
§ 371 (c)(1),
(2) Date: Jun. 10, 2022

(87) PCT Pub. No.: WO2021/122584
PCT Pub. Date: Jun. 24, 2021

(65) Prior Publication Data
US 2023/0020698 A1 Jan. 19, 2023

(30) Foreign Application Priority Data
Dec. 20, 2019 (DE) .................... 10 2019 220 361.2

(51) Int. Cl.
*C25B 15/08* (2006.01)
*C01B 3/50* (2006.01)
(Continued)

(52) U.S. Cl.
CPC ............ *C25B 15/081* (2021.01); *C01B 3/506* (2013.01); *C07C 29/1518* (2013.01); *C25B 1/04* (2013.01);
(Continued)

(58) Field of Classification Search
CPC ................ C07C 29/1518; C07C 31/04; C01B 2203/062; C01B 2203/061;
(Continued)

(56) References Cited

U.S. PATENT DOCUMENTS

2009/0307975 A1  12/2009  Wolf
2018/0086985 A1  3/2018  Von Olshausen
(Continued)

FOREIGN PATENT DOCUMENTS

CN  107567351 A  1/2018
CN  109415822 A  3/2019
(Continued)

OTHER PUBLICATIONS

Bailera, Manuel et al.:"Power to gas-oxyfuel boiler hybrid systems"; Elsevier; international journal of hydrogen energy; Jan. 1, 2015; pp. 10168-10175; XP 055791040; URL:http://dx.doi.org/10.1016/j.ijhydene.2.
(Continued)

*Primary Examiner* — Jafar F Parsa
(74) *Attorney, Agent, or Firm* — Wolter Van Dyke Davis, PLLC

(57) ABSTRACT

A power-to-X system for the utilization of off-gases, includes an electrolyzer for generating hydrogen H2 and oxygen O2, a unit, connected to the electrolyzer, for processing the hydrogen H2, for removing any remaining water H2O and oxygen O2 from the generated stream of hydrogen H2, a compressor, connected to the unit for processing the hydrogen H2, for compressing the hydrogen H2, and a
(Continued)

chemical reactor, connected to the compressor, for producing a synthesis gas consisting of hydrogen H2 and carbon dioxide CO2 that can be added. An oxy-fuel combustion system to which non-condensable off-gases from the chemical reactor and oxygen O2 from the electrolyzer can be supplied, and carbon dioxide CO2 generated during the combustion of the off-gases in the oxy-fuel combustion system can be returned to the stream of hydrogen H2 downstream of the electrolyzer via a return line.

20 Claims, 3 Drawing Sheets

(51) Int. Cl.
| | |
|---|---|
| *C07C 29/151* | (2006.01) |
| *C25B 1/04* | (2021.01) |
| *C25B 9/17* | (2021.01) |
| *F23G 5/46* | (2006.01) |
| *F23G 7/06* | (2006.01) |
| *F23J 15/02* | (2006.01) |
| *F23L 7/00* | (2006.01) |
| *F23N 5/00* | (2006.01) |

(52) U.S. Cl.
CPC .............. *C25B 9/17* (2021.01); *C25B 15/083* (2021.01); *C25B 15/085* (2021.01); *F23G 5/46* (2013.01); *F23G 7/06* (2013.01); *F23G 7/063* (2013.01); *F23L 7/007* (2013.01); *F23N 5/006* (2013.01); *C01B 2203/046* (2013.01); *C01B 2203/0495* (2013.01); *C01B 2203/061* (2013.01); *C01B 2203/062* (2013.01); *F23G 2209/14* (2013.01); *F23G 2209/26* (2013.01); *F23J 15/02* (2013.01)

(58) Field of Classification Search
CPC ....... C01B 2203/0495; C01B 2203/046; F23G 7/063; F23G 7/06; C25B 1/04; C25B 15/085
See application file for complete search history.

(56) References Cited

U.S. PATENT DOCUMENTS

| | | |
|---|---|---|
| 2019/0185396 A1 | 6/2019 | Schulz |
| 2021/0292260 A1 | 9/2021 | Hannemann et al. |

FOREIGN PATENT DOCUMENTS

| | | |
|---|---|---|
| DE | 102016213668 A1 | 2/2018 |
| EP | 2360230 A1 | 8/2011 |
| EP | 2491998 A1 | 8/2012 |
| WO | 2014087433 A1 | 6/2014 |
| WO | 2017102817 A1 | 6/2017 |

OTHER PUBLICATIONS

PCT International Search Report and Written Opinion of International Searching Authority mailed Apr. 14, 2021 corresponding to PCT International Application No. PCT/EP2020/086200 filed Dec. 15, 2020.

APPARATUS AND METHOD FOR UTILIZING OFF-GASES FROM A POWER-TO-X SYSTEM

CROSS REFERENCE TO RELATED APPLICATIONS

This application is the US National Stage of International Application No. PCT/EP2020/086200 filed 15 Dec. 2020, and claims the benefit thereof. The International Application claims the benefit of German Application No. DE 10 2019 220 361.2 filed 20 Dec. 2019. All of the applications are incorporated by reference herein in their entirety.

FIELD OF INVENTION

The invention relates to an apparatus and a method for utilizing off-gases which are formed in a power-to-X plant. One application of a power-to-X plant is, for example, the production of carbon-based substances, such as methanol or hydrocarbon. Power-to-X refers to different ways of utilizing or storing electrical energy, for example from renewable energy (e.g., sun, wind and hydropower).

BACKGROUND OF INVENTION

Some of these technologies are power-to-liquid/power-to-gas processes which may be a major element for decarbonization or defossilization of the transport and energy sector and which are also used for energy storage. In the transport sector, fossil fuels may thus be partially or completely replaced by electricity-based e-fuels in the future. Such carbon-based e-fuels are produced through synthesis of hydrogen and carbon dioxide.

Hydrogen is obtained by electrolysis using renewable electrical energy. The carbon dioxide can come from point sources, or can be obtained by removal by means of chemical or physical scrubbing, or from the air by means of adsorption processes. An example of such e-fuels is e-methanol, which can then, for example, be used directly or via admixtures for combustion engines. In addition, methanol is a starting material for many chemicals and can also be used for producing synthetic gasoline (e-gasoline). The starting material of conventional processes for producing methanol from fossil raw materials is synthesis gas, a mixture of predominantly hydrogen and carbon monoxide.

A power-to-X plant for converting regenerative energy into e-fuel essentially comprises an electrolyzer for production of hydrogen $H_2$ and oxygen $O_2$, a plant for processing of the hydrogen including drying of the hydrogen $H_2$ produced, a compressor for compression of the hydrogen $H_2$, and a chemical reactor for synthesis of, for example, methanol. The synthesis taking place in tube reactors cannot be carried out completely in one step. Therefore, the unreacted product stream is recycled into the chemical reactor.

So-called off-gas streams must be discharged from the process continuously or discontinuously in order to avoid concentration of noncondensable gases.

Major constituents of these off-gas streams are hydrogen $H_2$, carbon dioxide $CO_2$, carbon monoxide $CO$, methane $CH_4$ and methanol $CH_3OH$. Further off-gases are formed during processing of the crude methanol during distillation to separate water and methanol.

These off-gases are currently combusted with air. The air required for the combustion of the off-gases may have to be compressed by blowers for the combustion. The resulting combustion gas, predominantly $CO_2$, water $H_2O$ and nitrogen $N_2$, is released into the atmosphere. Utilization of the carbon dioxide $CO_2$ as a starting material for synthesis is thus not envisaged; it would require complicated removal from the combustion gas, preferably by chemical or physical scrubbing.

SUMMARY OF INVENTION

It is an object of the invention to provide a power-to-X plant which can utilize the off-gases economically and can avoid emission of carbon dioxide $CO_2$. It is a further object of the invention to specify a corresponding method for operating such a power-to-X plant for utilizing off-gases.

The object of the invention that is directed to an apparatus is achieved by a power-to-X plant for utilizing off-gases according to the features of the independent claim. It comprises an electrolyzer for production of hydrogen $H_2$ and oxygen $O_2$, a plant for processing of the hydrogen, connected to the electrolyzer, for separation of remaining oxygen $O_2$ and water $H_2O$ from the stream of hydrogen $H_2$ produced, at least one compressor for compression of the hydrogen $H_2$ or of the mixture of hydrogen $H_2$ and carbon dioxide $CO_2$, and a chemical reactor for production of a synthesis gas from hydrogen $H_2$ and suppliable carbon dioxide $CO_2$.

According to the invention, an oxyfuel combustion plant is further comprised, in which noncondensable off-gases from the chemical reactor and oxygen $O_2$ from the electrolyzer are suppliable, and carbon dioxide $CO_2$ which is formed in the oxyfuel combustion plant as a result of the combustion of the off-gases is recyclable via a return line into the stream of hydrogen $H_2$ downstream of the electrolyzer.

The invention is based on the consideration that the off-gases which are inevitably formed during the synthesis in the chemical reactor are thermally treated in an oxyfuel combustion plant downstream of the chemical reactor. The oxyfuel combustion plant is suitable for oxygen-based combustion. The thermal treatment is carried out with virtually pure oxygen $O_2$ as an oxidizer.

The invention recognizes that the oxygen must be formed anyway in the upstream electrolysis and usually cannot be further used anyway economically. The fact that this oxygen fraction may contain small traces of hydrogen is also not disadvantageous, since the hydrogen $H_2$ combusts to form pure water.

It is particularly advantageous that the combustion gas of the oxygen-based combustion consists almost entirely of water vapor and carbon dioxide $CO_2$. By comparatively simple condensation of the water vapor, the carbon dioxide $CO_2$ can be obtained in a very pure form and recycled to the production process.

In this way, the off-gas can advantageously be recycled into the power-to-X process and does not have to be combusted via an air-blown flare. In addition to the oxygen $O_2$ from the electrolysis, oxygen $O_2$ from a separate oxygen source can also be used, meaning that the apparatus according to the invention can also be integrated into existing systems in which oxygen $O_2$ occurs as process gas.

As a result of the combustion of the off-gases and recycling of the carbon dioxide $CO_2$ and further constituents into the production process, climate-damaging $CO_2$ emissions can be avoided. Complicated removal of carbon dioxide $CO_2$ from the off-gases, for example by chemical or physical scrubbing, can be omitted. Compared to conventional off-gas combustion using air, the invention may also save energy for an air blower, since there is no need to compress nitrogen $N_2$ as well.

In an advantageous development of the invention, the power-to-X plant further comprises a heat exchanger by means of which the heat generated during the combustion is dissipatable and is integrable into other parts of the power-to-X plant. In particular, the heat can be integrated into crude methanol processing or into auxiliary steam generation for start-up of the chemical reactor. The crude methanol contains water as a reaction product. In crude methanol processing, the methanol/water mixture is separated by distillation. The integration of the heat generated in the oxyfuel combustion plant into other parts of the power-to-X plant can increase the overall efficiency of the plant. In addition, this gives rise to additional ways of increasing flexibility, since the heat can also be used to keep components warm during a brief plant downtime.

In a further advantageous embodiment of the invention, biomass and/or processed waste for $CO_2$-neutral incineration is, alternatively or additionally, suppliable to the oxyfuel combustion plant and/or the oxyfuel combustion plant comprises a heater by means of which it is electrically heatable using electricity from renewable sources. Other combustible substances as well can be combusted in the oxyfuel combustion plant. In this way, the power-to-X plant can advantageously also be integrated into a waste incineration plant, sewage treatment plant or biomass plant or into corresponding processes. Preferably, off-gas or other residual gases from the power-to-X plant can, additionally or alternatively, also be combusted.

Preferably, the power-to-X plant comprises a removal flow line through which recirculated synthesis gas from the chemical reactor is suppliable to the oxyfuel combustion plant. Regulation of the stream of synthesis gas can advantageously support the combustion in the oxyfuel combustion plant.

In a further advantageous embodiment of the invention, a lambda probe is arranged in the combustion gas line of the oxyfuel combustion plant, so that, by measurement and regulation of a quantity of oxygen $O_2$ introduced, complete combustion of the off-gases and mixed gases to form $CO_2$ is ensured. What is measured is the oxygen content $O_2$ in the combustion gas, and what is then regulated is the stream of the quantity of oxygen $O_2$ introduced. What is avoided in particular by the regulation is a relevant excess of $O_2$ in the combustion gas, which might lead to problems concerning the purity of the stream of $CO_2$ produced. Alternatively or additionally, a catalytic reaction with hydrogen $H_2$ can remove the oxygen $O_2$ remaining in the removed stream of $CO_2$.

In an advantageous embodiment of the invention, the $H_2/CO_2$ synthesis gas is compressed using a piston compressor to operating pressures above 10 bar. Owing to the operating pressure of the piston compressor that is chosen, subsequent drying (condensation of $H_2O$) and $O_2$ removal (DeOxoDryer) can be carried out cost-effectively. Because of the higher inlet pressure and the proportion of carbon dioxide $CO_2$, the compressor can, alternatively, also be designed as a turbo compressor. The stream of hydrogen from the electrolysis contains water vapor and small quantities of oxygen. The oxygen is catalytically reacted with hydrogen to form water, which is then removed as a whole by condensation.

In a particular embodiment of the invention, the power-to-X plant further comprises a return line for carbon dioxide $CO_2$ through which the carbon dioxide $CO_2$ from the oxyfuel combustion plant is suppliable into the line for hydrogen $H_2$ upstream of the compressor. The return line is connected into the line for hydrogen $H_2$ between electrolyzer and compressor. This embodiment takes into account that the carbon dioxide $CO_2$ additionally contains further gases, which are added together as combustion gas to the stream of hydrogen $H_2$ downstream of the electrolysis and upstream of the compression. This is possible because water vapor and residual oxygen $O_2$ are contained in the stream of hydrogen downstream of the electrolysis and the combustion gas contains only small quantities of oxygen $O_2$.

In a further advantageous development, the power-to-X plant further comprises a contaminant remover which is connected to the oxyfuel combustion plant and in which contaminants produced in the oxyfuel process, such as sulfur, alkali-metal and halogen compounds, and oxygen $O_2$ are removable. This is sensible if, for example, biomass is additionally supplied to the oxyfuel combustion plant. The oxygen $O_2$ in particular is removable cryogenically. The purified carbon dioxide $CO_2$ is suppliable via a return line to the stream of hydrogen $H_2$ upstream of the compressor. This remover is particularly advantageous because the carbon dioxide $CO_2$ produced in the oxyfuel process is contaminated with sulfur, alkali-metal and halogen compounds and contains relatively large quantities of oxygen $O_2$ that must be removed before addition to the hydrogen $H_2$.

The object of the invention that is directed to a method is achieved by a method for utilizing off-gases in a power-to-X plant as claimed.

In the method according to the invention, hydrogen $H_2$ and oxygen $O_2$ are produced by an electrolyzer, remaining water $H_2O$ and oxygen $O_2$ are separated from the hydrogen $H_2$ in a plant for processing of the hydrogen, the hydrogen $H_2$ is compressed in at least one compressor for compression of the hydrogen $H_2$ or of the mixture of hydrogen $H_2$ and carbon dioxide $CO_2$, and alcohols or hydrocarbons are produced in a chemical reactor. According to the invention, the noncondensable off-gases from the chemical reactor together with oxygen $O_2$ from the electrolyzer are supplied to an oxyfuel combustion plant, and carbon dioxide $CO_2$ which is formed as a result of the combustion of the off-gases is recycled into the stream of hydrogen $H_2$ downstream of the electrolyzer. The advantages of the above-described apparatus according to the invention apply equally to the method according to the invention.

In an advantageous development, the oxyfuel combustion plant further comprises a heat exchanger by means of which the heat generated during the combustion is dissipated and is integrated into other parts of the power-to-x plant. In particular, the heat can be transferred to crude methanol processing and/or to auxiliary steam generation for start-up of the chemical reactor.

In a particular embodiment of the method, biomass and/or processed waste for $CO_2$-neutral incineration is, alternatively or additionally, combusted in the oxyfuel combustion plant. Additionally or alternatively, the oxyfuel combustion plant further comprises a heater by means of which it is electrically heated using electricity from renewable sources. Additionally or alternatively, off-gas or the residual gases from the power-to-X plant can also be supplied to the oxyfuel combustion plant.

As part of an advantageous development, synthesis gas from the chemical reactor is supplied to the oxyfuel combustion plant via a removal flow line in order to support the combustion process in the oxyfuel combustion plant.

In a particular development of the method, the oxygen concentration in the oxyfuel combustion plant is measured by a lambda probe in the combustion gas line, and complete combustion of the mixed gases to form $CO_2$ is ensured by regulation of the quantity of oxygen $O_2$ introduced.

In an advantageous embodiment of the method according to the invention, the compressor is a piston compressor which is operated at a pressure of above 10 bar, and the plant for processing of the hydrogen $H_2$ is a DeOxoDryer.

Advantageously, the carbon dioxide $CO_2$ from the oxyfuel combustion plant is supplied through a return line for carbon dioxide $CO_2$ into the line for hydrogen $H_2$ upstream of the compressor.

In a further particular development of the invention, the contaminants produced in the oxyfuel process, such as sulfur, alkali-metal and halogen compounds, and oxygen $O_2$ are removed in a contaminant remover, wherein the oxygen $O_2$ in particular is removed cryogenically, and the purified carbon dioxide $CO_2$ is supplied into the stream of hydrogen $H_2$ via a return line upstream of the compressor.

BRIEF DESCRIPTION OF THE DRAWINGS

The invention is described in more detail in the text which follows with reference to figures. In the figures.

DETAILED DESCRIPTION OF INVENTION

Figure 1:
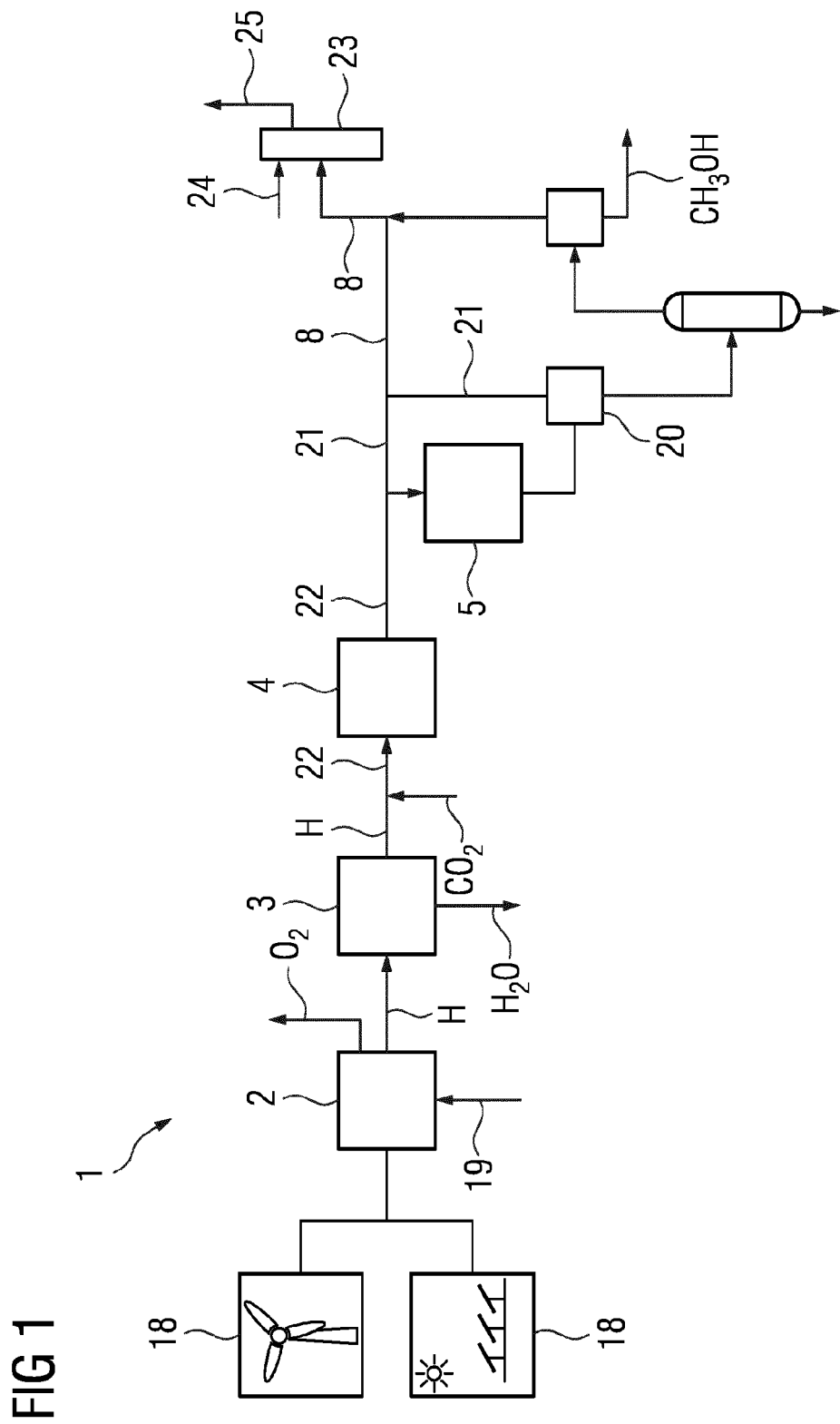
FIG. 1 shows a power-to-X plant according to the prior art.

FIG. 1 shows a power-to-X plant 1 according to the prior art. It essentially consists of an electrolyzer 2, a plant for processing of hydrogen 3, a compressor 4, and a chemical reactor 5 for methanol synthesis.

What is supplied to the electrolyzer 2 is regenerative electrical energy 18 which, for example, comes from a wind turbine or photovoltaic system. Moreover, water 19 is supplied to the electrolyzer 2. In the electrolyzer, hydrogen $H_2$ and oxygen $O_2$ are produced. The oxygen $O_2$ is released into the atmosphere and the hydrogen $H_2$ is conducted into the plant for processing 3 for drying. The hydrogen $H_2$ is withdrawn from and conducted out of the plant for processing of the hydrogen 3. The hydrogen $H_2$ dried in the plant 3 is conducted out of the plant 3 and mixed with carbon dioxide $CO_2$, which is supplied to the power-to-X plant from outside.

The hydrogen $H_2$/carbon dioxide $CO_2$ mixture is also referred to as synthesis gas 22. The synthesis gas 22 is then supplied to the compressor 4 and is compressed therein. The compressed synthesis gas 22 is then conducted into the chemical reactor 5, where it is starting material for the synthesis of methanol. The conversion of synthesis gas 22 into methanol takes place in tubular reactors and is not complete in one step. Downstream of the chemical reactor 5 is a gas-liquid separation plant 20, in which the partially converted product (methanol and water) is withdrawn. The incompletely converted partial stream 21 is recycled into the chemical reactor 5 and thus circulated.

As a result of the reaction in the chemical reactor 5, what are formed are not only methanol, but also further noncondensable gases, which are concentrated in the chemical reactor 5 owing to the circulation. Major constituents are hydrogen $H_2$, carbon dioxide $CO_2$, carbon monoxide CO, methane $CH_4$ and methanol $CH_3OH$. These gas mixtures are referred to as off-gases 8, which are discharged from the process continuously or discontinuously in order to avoid excessively high concentration of noncondensable gases in the chemical reactor 5.

In the prior art, these off-gases 8 are supplied to a combustion plant 23 and combusted under supply of air 24. What is formed here is a combustion gas 25 which predominantly contains carbon dioxide $CO_2$, water $H_2O$ and nitrogen $N_2$ and which is released into the atmosphere.

Leaving the power-to-X plant is synthetically produced methanol $CH_3OH$.

Figure 2:
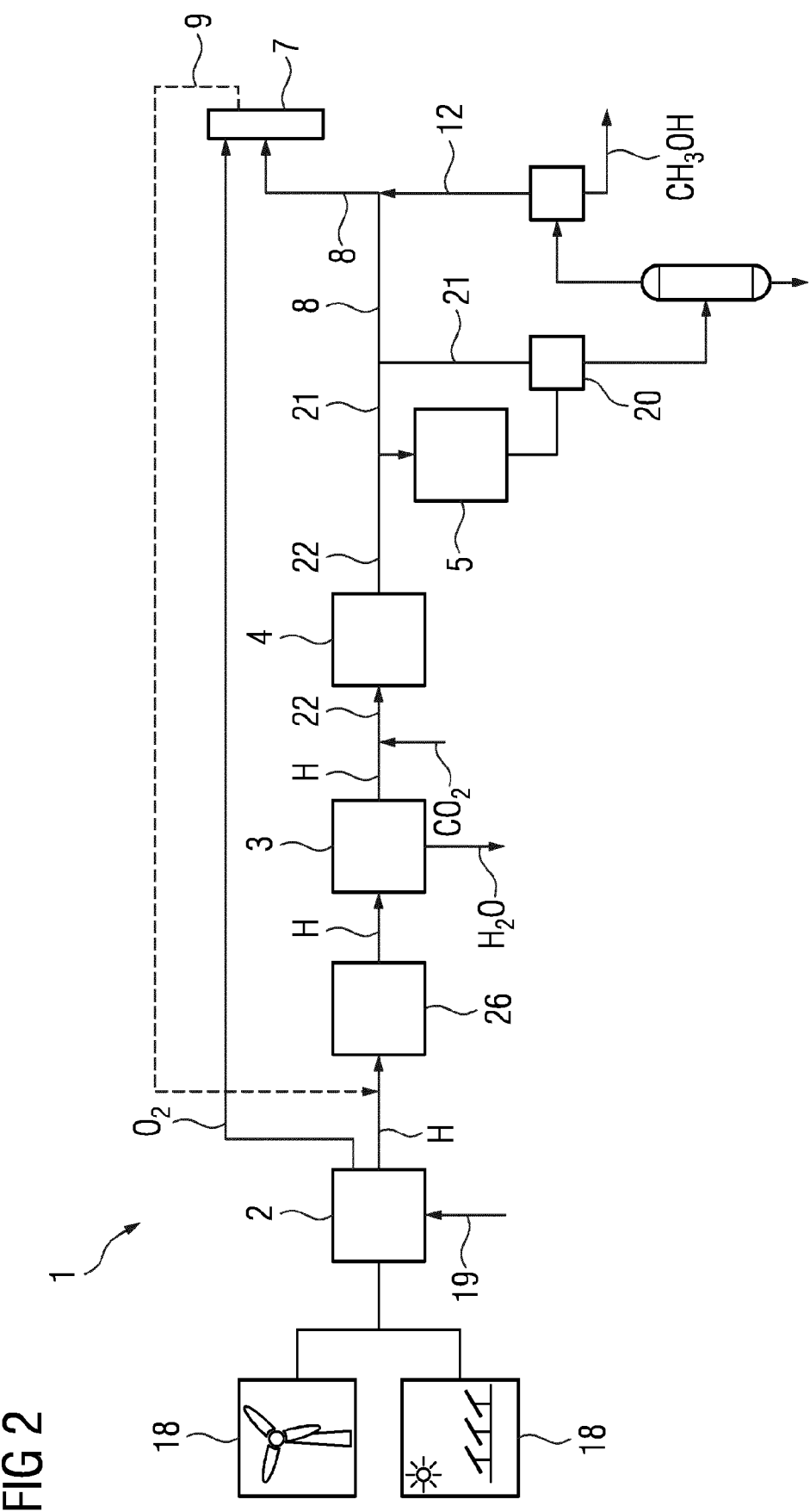
FIG. 2 shows a power-to-X plant according to a first embodiment of the invention.

FIG. 2 shows a power-to-X plant according to a first embodiment of the invention. In contrast to FIG. 1, the oxygen $O_2$ produced in the electrolyzer 2 is not released, or not completely released, into the atmosphere, but diverted for use later in the process. In a further difference from the prior art, there is provided a further compressor 26, which is arranged upstream of the plant for processing of the hydrogen 3. The central difference from the prior art is the provision of an oxyfuel combustion plant 7, to which the oxygen $O_2$ from the electrolyzer 2 and the off-gas 8 from the chemical reactor 5 are supplied.

In the oxyfuel combustion plant 7, the off-gases 8 are likewise utilized thermally, but with virtually pure oxygen $O_2$ as an oxidizer that has been removed from the electrolyzer 2 as a by-product. The combustion gas of the oxygen-based combustion consists almost entirely of water vapor and carbon dioxide $CO_2$. By comparatively simple condensation of the water vapor, the carbon dioxide $CO_2$ can be obtained in a very pure form and recycled to the production process.

According to the invention, the combustion gas consisting of virtually pure carbon dioxide $CO_2$ is recycled via a return line 9 into the stream of hydrogen $H_2$ downstream of the electrolyzer 2. The recycling is expediently carried out upstream of the compressor 26.

In order to support the combustion in the oxyfuel combustion plant 7, there is further provided a removal flow line 12 through which synthesis gas from the chemical reactor 5 is suppliable to the oxyfuel combustion plant 7.

In the power-to-X plant 1 according to FIG. 2, a lambda probe 14 can be arranged in the return line 9 of the oxyfuel combustion plant 7, so that, by measurement and regulation of a quantity of oxygen $O_2$ introduced, complete combustion of the off-gases to form $CO_2$ is ensured without, however, supplying oxygen in excess.

The compressor 4 can be designed as a piston compressor designed for operating pressures above 10 bar. The plant for processing of the hydrogen 3 can be a DeOxoDryer.

Figure 3:
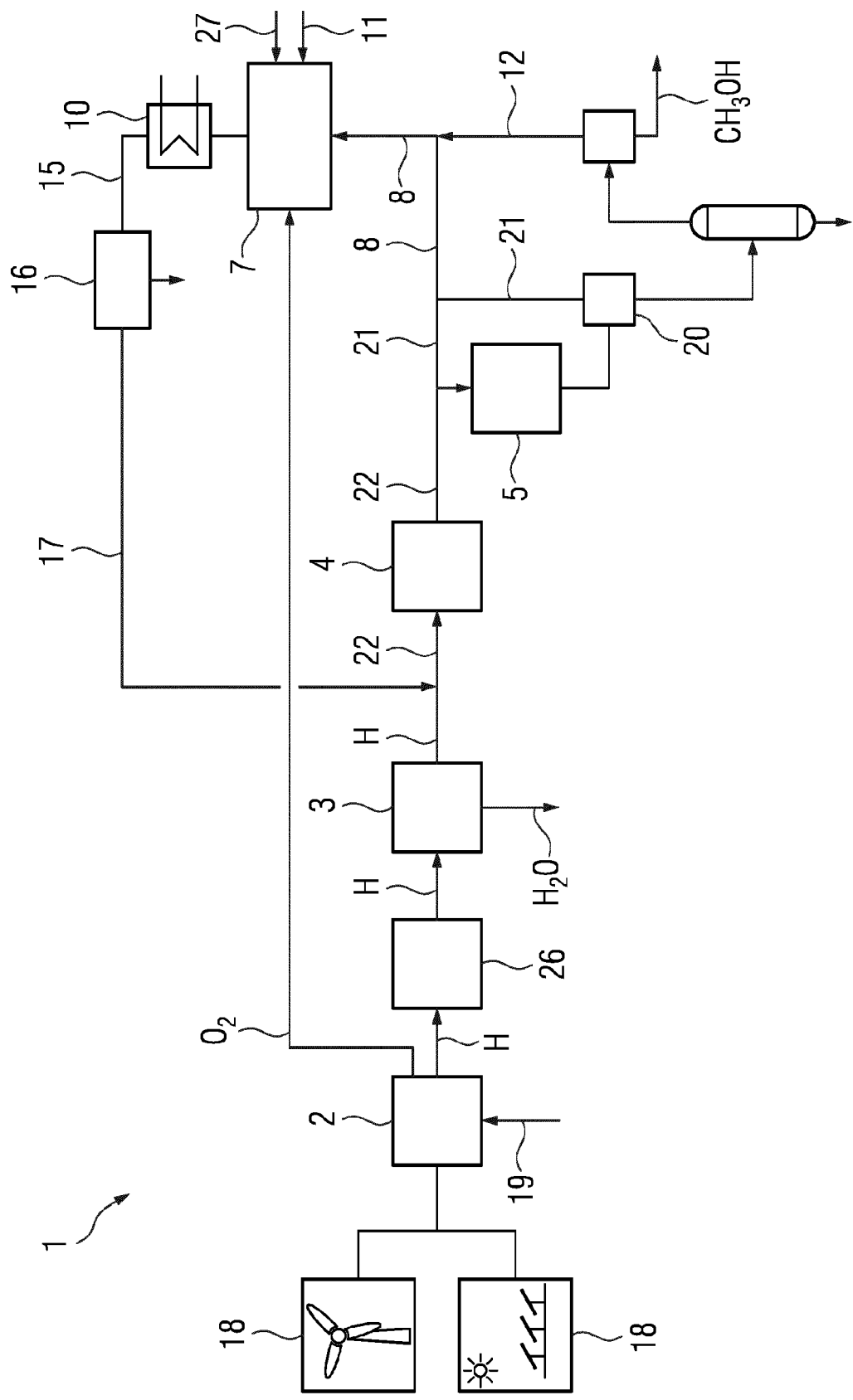
FIG. 3 shows a power-to-X plant according to a further embodiment of the invention.

FIG. 3 shows an alternative embodiment of the invention. The essential difference from the embodiment in FIG. 2 is that the oxyfuel combustion plant 7 is an oxyfuel boiler, to which, alternatively or additionally, biomass and/or processed waste 27 is supplied. Alternatively or additionally, what can be provided in the oxyfuel combustion plant 7 is a heater 11 which is electrically heatable using electricity from renewable sources.

Moreover, there is provided a heat exchanger 10 which is downstream of the oxyfuel combustion plant 7. It is by means of the heat exchanger 10 that the heat generated during the combustion is dissipatable and is integrable into other parts of the power-to-X plant 1. The heat can advantageously be transferred to crude methanol processing and/or to auxiliary steam generation for start-up of the chemical reactor 5.

Connected to the oxyfuel combustion plant 7 of FIG. 3 is a return line for carbon dioxide $CO_2$ 15 through which the carbon dioxide $CO_2$ can be conducted out of the oxyfuel combustion plant. Connected into the return line 15 is a contaminant remover 16 which removes contaminants produced in the oxyfuel process, such as sulfur, alkali-metal and halogen compounds, and relatively large quantities of oxygen $O_2$. The oxygen $O_2$ in particular is removed cryogenically. The stream of largely pure carbon dioxide $CO_2$ that has been purified by the remover 16 is supplied via a return line 17 to the stream of hydrogen $H_2$ upstream of the compressor 4.

The invention makes it possible to utilize the off-gases which are formed in a power-to-X plant for the process, instead of having to release them into the atmosphere. This makes it possible to reduce the emission of $CO_2$ from the entire plant while simultaneously utilizing the carbon dioxide $CO_2$ in the actual process and the oxygen $O_2$ from the electrolyzer. Compared to conventional off-gas combustion, energy for the air blowers can also be saved as a result.

The invention claimed is:

1. A power-to-X plant for utilizing off-gases, comprising:
    an electrolyzer for production of hydrogen $H_2$ and oxygen $O_2$,
    a plant for processing of the hydrogen, connected to the electrolyzer, for separation of remaining oxygen $O_2$ and water $H_2O$ from a stream of hydrogen $H_2$ produced,
    at least one compressor for compression of the hydrogen $H_2$ or of a mixture of hydrogen $H_2$ and carbon dioxide $CO_2$,
    a chemical reactor for production of alcohols or hydrocarbons, and
    an oxyfuel combustion plant, to which noncondensable off-gases from the chemical reactor and oxygen $O_2$ from the electrolyzer are supplied, and carbon dioxide $CO_2$ which is formed in the oxyfuel combustion plant as a result of the combustion of the off-gases is recycled via a return line into the stream of hydrogen $H_2$ downstream of the electrolyzer.

2. The power-to-X plant as claimed in claim 1, wherein the oxyfuel combustion plant comprises a heat exchanger by which the heat generated during the combustion is dissipated and is integrated into other parts of the power-to-X plant.

3. The power-to-X plant as claimed in claim 1, wherein biomass and/or processed waste is, alternatively or additionally, supplied to the oxyfuel combustion plant and/or the oxyfuel combustion plant comprises a heater by which it is electrically heated using electricity from renewable sources.

4. The power-to-X plant as claimed in claim 1, further comprising:
    a removal flow line through which synthesis gas from the chemical reactor is supplied to the oxyfuel combustion plant.

5. The power-to-X plant as claimed in claim 1, wherein a lambda probe is arranged in the return line of the oxyfuel combustion plant, so that, by measurement and regulation of a quantity of oxygen $O_2$ introduced, complete combustion of the off-gases to form $CO_2$ is ensured.

6. The power-to-X plant as claimed in claim 1, wherein the compressor for compression of hydrogen $H_2$ and carbon dioxide $CO_2$ is a piston compressor designed for operating pressures above 10 bar, and the plant for processing of the hydrogen is a DeOxoDryer.

7. The power-to-X plant as claimed in claim 1, further comprising:
    a return line for carbon dioxide $CO_2$ through which the carbon dioxide $CO_2$ from the oxyfuel combustion plant is supplied into the stream for hydrogen $H_2$ upstream of the compressor.

8. The power-to-X plant as claimed in claim 1, further comprising:
    a contaminant remover which is connected to the oxyfuel combustion plant and in which contaminants produced in the oxyfuel process, are removed, and the purified carbon dioxide $CO_2$ is supplied via a return line to the stream of hydrogen $H_2$ upstream of the compressor.

9. A method for utilizing off-gases in a power-to-X plant, comprising:
    producing hydrogen $H_2$ and oxygen $O_2$ by an electrolyzer,
    separating remaining water $H_2O$ and oxygen $O_2$ from the hydrogen $H_2$ in a plant for processing of the hydrogen,
    compressing the hydrogen $H_2$ in a compressor,
    producing synthesis gas in a chemical reactor from the hydrogen $H_2$ together with carbon dioxide $CO_2$, and
    supplying noncondensable off-gases, contained in the synthesis gas, from the chemical reactor together with oxygen $O_2$ from the electrolyzer are supplied to an oxyfuel combustion plant, and carbon dioxide $CO_2$ which is formed as a result of the combustion of the off-gases is recycled into the stream of hydrogen $H_2$ downstream of the electrolyzer.

10. The method as claimed in claim 9, wherein the oxyfuel combustion plant comprises a heat exchanger by which the heat generated during the combustion is dissipated and is integrated into other parts of the power-to-X plant.

11. The method as claimed in claim 9, wherein biomass and/or processed waste for incineration is, alternatively or additionally, combusted in the oxyfuel combustion plant and/or wherein the oxyfuel combustion plant comprises a heater by which it is electrically heated using electricity from renewable sources.

12. The method as claimed in claim 9, wherein synthesis gas from the chemical reactor is supplied to the oxyfuel combustion plant via a removal flow line.

13. The method according to claim 9, wherein the oxygen concentration in the oxyfuel combustion plant is measured by a lambda probe in a return line, and complete combustion of the mixed gases to form $CO_2$ is ensured by regulation of the quantity of oxygen $O_2$ introduced.

14. The method as claimed in claim 9, wherein the compressor is a piston compressor which is operated at a pressure of above 10 bar and wherein the plant for processing of the hydrogen is a DeOxoDryer.

15. The method as claimed in claim 9, wherein the carbon dioxide $CO_2$ from the oxyfuel combustion plant is supplied through a return line for carbon dioxide $CO_2$ into the line for hydrogen $H_2$ upstream of the compressor.

16. The method as claimed in claim 9, wherein contaminants produced in the oxyfuel process, are removed in a contaminant remover, and the purified carbon dioxide $CO_2$ is supplied into the stream of hydrogen $H_2$ via a return line upstream of the compressor.

17. The power-to-X plant as claimed in claim 2,
wherein the heat generated during the combustion is dissipated and is integrated into crude methanol processing and/or into auxiliary steam generation for start-up of the chemical reactor.

18. The power-to-X plant as claimed in claim 8,
wherein the oxygen O2 is removed cryogenically.

19. The method as claimed in claim 10,
wherein the heat generated during the combustion is dissipated and is integrated into crude methanol processing and/or into auxiliary steam generation for start-up of the chemical reactor.

20. The method as claimed in claim 16,
wherein the oxygen O2 is removed cryogenically.

\* \* \* \* \*